(12) United States Patent
Konzelmann et al.

(10) Patent No.: US 7,467,541 B2
(45) Date of Patent: Dec. 23, 2008

(54) SENSOR HAVING A THERMAL GRADIENT PUMP

(75) Inventors: Uwe Konzelmann, Asperg (DE); Ulrich Wagner, Stuttgart (DE); Christoph Gmelin, Stuttgart (DE); Martin Baumann, Fellbach (DE)

(73) Assignee: Robert Bosch GmbH, Stuttgart (DE)

( * ) Notice: Subject to any disclaimer, the term of this patent is extended or adjusted under 35 U.S.C. 154(b) by 133 days.

(21) Appl. No.: 11/603,574

(22) Filed: Nov. 22, 2006

(65) Prior Publication Data

US 2007/0144239 A1 Jun. 28, 2007

(30) Foreign Application Priority Data

Dec. 9, 2005 (DE) .................. 10 2005 058 830

(51) Int. Cl.
*G01N 25/18* (2006.01)

(52) U.S. Cl. ............... 73/25.01; 73/25.05; 73/31.05
(58) Field of Classification Search .............. 73/25.01, 73/25.05, 23.2, 23.31, 31.05
See application file for complete search history.

(56) References Cited

U.S. PATENT DOCUMENTS

| 6,202,467 | B1 * | 3/2001 | Iovdalsky et al. ........... 73/23.2 |
| 6,978,611 | B1 * | 12/2005 | Landis ........................ 60/513 |

FOREIGN PATENT DOCUMENTS

| DE | 196 01 791 | 7/1997 |
| DE | 101 11 840 | 10/2002 |

* cited by examiner

*Primary Examiner*—Daniel S Larkin
(74) *Attorney, Agent, or Firm*—Kenyon & Kenyon LLP

(57) ABSTRACT

A sensor for detecting a component of a gaseous fluid containing multiple components. The sensor includes a housing, which delimits a measuring chamber and which accommodates a measuring chip having a heatable diaphragm. The housing has at least one opening which allows convective heat transport.

7 Claims, 2 Drawing Sheets

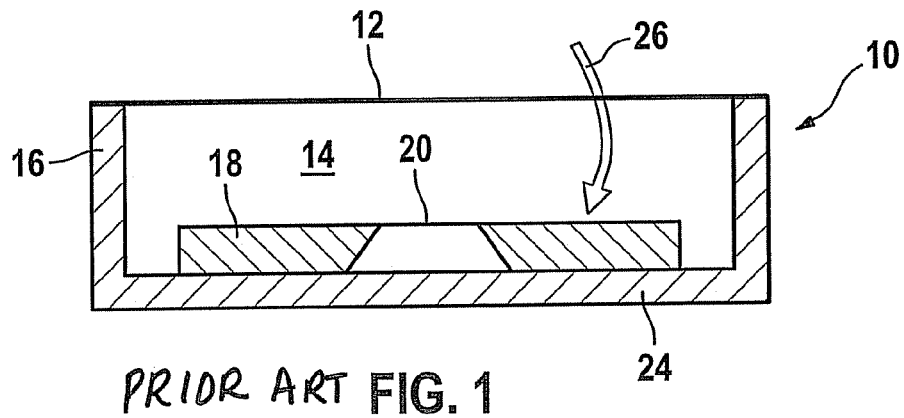
PRIOR ART FIG. 1
FIG. 2 PRIOR ART
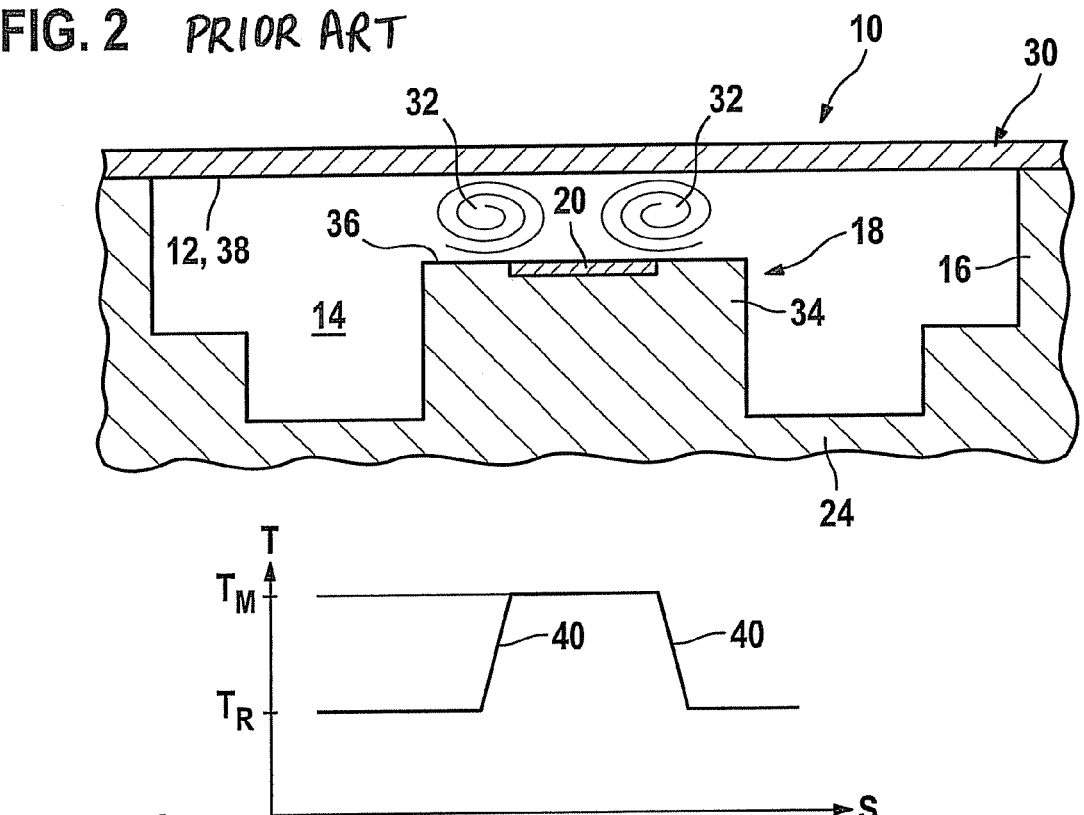
FIG. 2.1

SENSOR HAVING A THERMAL GRADIENT PUMP

BACKGROUND INFORMATION

A type of sensor for detecting the temperature of a gaseous fluid is, for example, a hot-film air mass meter (HFM), which is described, for example, in German Patent Application No. DE 196 01 791. In hot-film air mass meters of this type, a thin sensor diaphragm is typically applied to a sensor chip, which is preferably a silicon sensor chip. At least one heating resistor, which is enclosed by two or more temperature measuring resistors, is typically situated on the sensor diaphragm. The temperature distribution which may in turn be detected by the temperature measuring resistors changes in an air flow which is guided over the diaphragm. Thus, for example, an air mass flow may be determined from the resistance differential of the temperature measuring resistors. Various other variations of this sensor type are known from the related art. A sensor chip, which has a frame element manufactured from silicon, having a diaphragm applied thereto, is described in German Patent No. DE 101 11 840. Various metal webs which function as electrical heaters and/or measuring resistors are situated on the diaphragm, resulting in the area of the diaphragm forming a sensor area. Moreover, at least one auxiliary heater which may be electrically heated in such a way that thermal gradient eddies are formed in the flowing medium in the area of the auxiliary heater may additionally be situated on the surface of the sensor chip.

In addition to the detection of the temperature of a gaseous fluid, the detection of components of which the particular gaseous fluid is composed plays a large role. To detect hydrogen, for example, the property of hydrogen of having significantly better thermal conductivity than air, for example, is exploited. In a sensor construction which has a similar design to that of hot-film air mass meters (HFM), an air-hydrogen mixture, for example, diffuses through a thin diaphragm or a tight grid into the measuring chamber of a sensor. The presence of hydrogen in the gaseous fluid changes the temperature of the heated measuring diaphragm or its thermal output, which is delivered to the surrounding air. A measurement signal is in turn generated therefrom. These sensors are typically operated at measuring chip and/or housing temperatures which approximately correspond to room temperature (25° C.). The diaphragms used in the sensors are typically operated at higher temperatures than the measuring chip or housing temperature, between 80 K and 120 K. These measuring sensors have the disadvantage of the moisture component contained in the gaseous fluid. The moisture contained in the gaseous fluid influences the thermal conductivity of the gaseous fluid, e.g., a hydrogen-air mixture. At room temperature, approximately 25° C., the influence of the moisture component contained in the gaseous fluid may be so large that detection of hydrogen by the sensor is no longer possible with the required clarity.

In diffusive processes, the thermal conductivity of the gaseous fluid dominates the heat transmission, while in conductive heat exchange processes, i.e., when fresh air is supplied, the heat capacity of the gaseous fluid is decisive for the resulting heat transmission. The atmospheric moisture contained in the gaseous fluid influences both heat transmission mechanisms, the thermal capacity of the gaseous fluid rising and its thermal conductivity sinking in the event of increasing moisture. The heat transmission and thus the heat flow are influenced in accordance with the proportions of diffusion and convection in the heat transmission process.

SUMMARY OF THE INVENTION

An object of the present invention is to compensate the influence of atmospheric moisture contained in a gaseous fluid by causing a defined convection.

It is suggested according to the present invention that the atmospheric moisture contained in the gaseous fluid will not influence the measurement result obtained in a sensor for detecting a component of a gaseous fluid containing multiple components because a suitable ratio is set between convection and diffusion during heat transmission.

In sensors which have a heated measuring diaphragm, a strong temperature gradient develops on the measuring diaphragm because of its heating. The gaseous fluid in direct proximity to the surface of a measuring chip is transported from cold to hot points by thermal creep. Thermal gradient eddies develop on both sides of the heated measuring diaphragm because of the existing temperature gradient. If the measuring chamber is closed by a lid having diaphragm properties, $H_2$ diffuses through this diaphragm into the measuring chamber in which the sensor is located.

In this case, the process of heat transmission is clearly dominated by diffusion in a measuring chip provided with a closed lid or cover.

It has been found according to the present invention that the thermal gradient eddies and the particle movement resulting therefrom on the surface of the measuring chip may be used for the purpose of causing a convection process in a targeted way and compensating for the influence of the moisture which is contained in the gaseous fluid via this convection process. The convection process along the measuring chip is caused by passing a flow of the gaseous fluid over the top side of the measuring diaphragm. Openings, which may be implemented as horizontally running channels, for example, are introduced in a targeted way in the sensor housing.

Fresh gaseous fluid enters a cavity enclosed by the housing through the openings formed laterally in the housing and leaves this cavity again via the cited opening formed centrally in the housing roof. Because of the openings formed in the sensor housing, fresh gaseous fluid enters a measuring chamber delimited by the housing and subsequently flows out through the central opening in the housing roof surface because of the heating. A convection flow which represents the dominant transport mechanism in the sensor according to the present invention is thus achieved. The proportions of the convection process and the diffusion process may be adjusted in relation to the total heat transmission in accordance with the design and the position of the openings in the housing and a moisture compensation may be predefined.

BRIEF DESCRIPTION OF THE DRAWINGS

FIG. 1 shows a cross section of a sensor for detecting a component of a gaseous fluid known from the related art.

FIG. 2 shows the closed housing of the sensor shown in FIG. 1.

FIG. 2.1 shows the temperature curve of the measuring diaphragm plotted over the extension of the measuring diaphragm.

DETAILED DESCRIPTION

Figure 3:
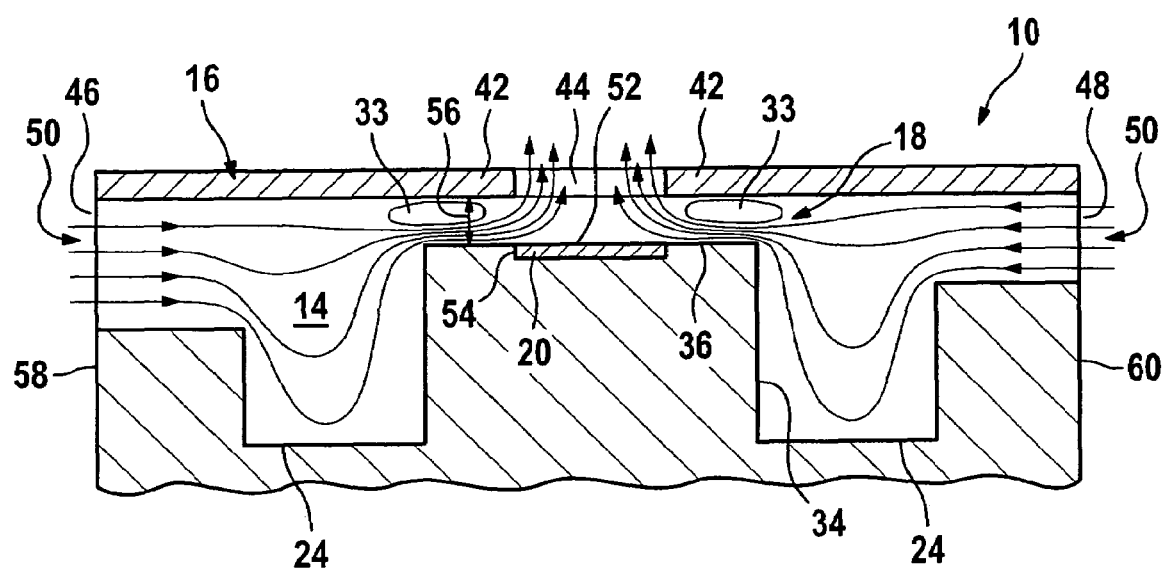
FIG. 3 shows a section of the housing of the sensor, implemented as suggested according to the present invention, for detecting a component of a gaseous fluid.

The illustration in FIG. 1 shows a section of a sensor known from the related art for detecting one component of a gaseous fluid containing multiple components.

A housing 16 of a sensor 10 is closed on the top side of housing 16 by a lid 12. Housing 16 and lid 12 delimit a measuring chamber 14 which accommodates a measuring chip 18. A heatable diaphragm 20 is located on measuring chip 18. Measuring chip 18 is fixed inside housing 16 on a housing floor 24. A gaseous fluid 26 which is, for example, a gaseous fluid 26 containing hydrogen, air, and an arbitrarily resulting atmospheric moisture diffuses through the cover of housing 16, implemented as lid 12.

The illustration in FIG. 2 shows a simplified sectional illustration of the housing of the sensor from FIG. 1.

It is apparent from the illustration in FIG. 2 that a chip socket 34, which accommodates measuring chip 18, projects out of housing floor 24 of housing 16. Chip-socket 34 has a-chip socket surface 36, into-which-heatable diaphragm 20, the measuring diaphragm, is introduced in a flush manner. A strong temperature gradient develops on its surface due to heatable diaphragm 20. Because of this temperature gradient, gaseous fluid in direct wall proximity is transported from cold points to hot points by thermal creep. In the embodiment variation illustrated in FIG. 2, housing 16 is a closed housing 30, which only lets through gaseous fluid 26 diffusing into measuring chamber 14. Because of heated diaphragm 20, thermal gradient eddies, identified by reference numeral 32, develop above heatable diaphragm 20. Since housing 16 is a closed housing 30, the heat exchange procedure is dominated by diffusion, since gaseous fluid 26 (compare the illustration in FIG. 1) only enters measuring chamber 14 through lid 12 of closed housing 30 because of diffusion.

The illustration in FIG. 2.1 shows the resulting temperature curve on the heatable diaphragm, plotted over the extension of the diaphragm in the plane of the drawing.

The temperature of heatable diaphragm 20, identified in FIG. 2.1 by $T_M$, assumes its maximum in the central area. The temperature curves illustrated as a ramp 40 indicate that heatable diaphragm 20, i.e., the measuring diaphragm, has a lower temperature, namely room temperature $T_R$, in its boundary areas at the transitions to chip socket surface 36. Thermal gradient eddies 32 illustrated in FIG. 2 result above heatable diaphragm 20 because of the high temperature gradient.

The illustration of FIG. 3 shows a housing having openings, via which a heat transmission process based both on convection and diffusion is achieved.

In the embodiment of the present invention illustrated in FIG. 3, sensor 10 includes a housing 16, which has an opening 44 in sensor housing lid 42, and which has at least one inflow opening 46, 48 on at least one housing side 58, 60. If sensor housing 16 has a square or rectangular outline, a first lateral inflow opening 46 and a second lateral inflow opening 48 may be implemented in housing 16 both on a first housing side 58 and also on a second housing side 60. If sensor housing 16 has a circular cross section and is delimited by a cylindrical mantle surface, inflow openings may be implemented in this surface at an angular offset of 90°, 120°, or 180° in relation to one another, which allow inflow of fresh gaseous fluid 50 to chip socket 34. Because heatable diaphragm 20 represents a heat source, a higher temperature exists above heatable diaphragm 20 introduced into a fitting 54 than next to chip socket 34 in measuring chamber 14. Because of the higher temperature in the area above heatable diaphragm 20, convection is generated nearly independently of the location in measuring chamber 14 by the thermal gradient eddies. The achieved heat transport is thus based on the diffusion of gaseous fluid 26 through lid surface 4242 of housing 16, composed as a diaphragm, for example, and also by convection heat transport, caused by both inflow openings 46 and 48 implemented laterally on the housing in FIG. 3.

Sensor housing lid 42, which has openings 44 in its central area, also allows diffusion of gaseous fluid 26 through its structure, composed as a diaphragm, for example. Thermal gradient eddies 33, which still result above heatable diaphragm 20, are thus "unfolded" and allow the flow of gaseous fluid 50 through opening 44 in sensor housing lid 42. In the illustration in FIG. 3, the residues of the thermal gradient eddies, which are less pronounced than in the illustration in FIG 2, are identified by reference numeral 33.

As a result of the achievement of the object according to the present invention, the heat transmission process has both a diffusive component and a convective component and the influence of the atmospheric moisture contained in gaseous medium 26, 50 may be suppressed because of the convective component of the heat transmission process. Since the atmospheric moisture influences both the diffusive process and the convective process, in which the heat capacity of gaseous fluid 26, 50 is decisive, a change of the resulting heat flow which is a function of the atmospheric moisture may be compensated for by a corresponding convective component in the heat transmission process. Because the atmospheric moisture of gaseous fluid 26, 50 is not to influence the measurement result, the component of the convective process is selected accordingly. The proportion of the convective process and the proportion of the diffusive process of the heat transfer procedure may be set and thus predefined by both corresponding dimensioning of opening 44 in sensor housing lid 42 and corresponding dimensioning of lateral inflow openings 46 and 48. The particle movement on the surface of heatable diaphragm 20, which represents the measuring diaphragm, may be exploited by openings 44,46, and 48, which are provided according to the present invention and implemented in housing 16 of sensor 10, to generate a convective flow of fresh gaseous fluid 50 over heatable diaphragm 20, via which the influence of the atmospheric moisture on the obtained signal may be reduced and entirely excluded, since the thermal capacity of gaseous fluid 26, 50 is decisive for the heat transmission in the event of convective heat transport.

What is claimed is:

1. A sensor for detecting a component of a gaseous fluid containing multiple components, comprising:

a measuring chamber;

a measuring chip having a heatable diaphragm; and a housing delimiting the measuring chamber, the housing accommodating the measuring chip, the housing having at least one opening which allows convective heat transport;

wherein the heatable diaphragm is situated on a socket-shaped elevation in the measuring chamber.

2. The sensor according to claim 1, wherein a top side of the housing has a sensor housing lid, in which an opening is situated.

3. The sensor according to claim 1, wherein at least one inflow opening for fresh gaseous fluid is situated in the housing on at least one housing side.

4. A sensor for detecting a component of a gaseous fluid containing multiple components, comprising:

a measuring chamber;

a measuring chip having a heatable diaphragm; and a housing delimiting the measuring chamber, the housing accommodating the measuring chip, the housing having at least one opening which allows convective heat transport;

wherein a top side of the housing has a sensor housing lid, in which an opening is situated; and wherein parts of the sensor housing lid extending from the opening with a top side of a socket-shaped elevation form an inflow area for fresh gaseous fluid flowing into the measuring chamber.

5. The sensor according to claim 1, wherein the sensor is for detecting $H_2$ in an $H_2$-air-$H_2O$ gas mixture.

6. A method for detecting a component in a gaseous fluid containing multiple components using a sensor, wherein a heat transmission from the gaseous fluid to a heatable diaphragm includes a diffusive heat transmission component and a dominant convective heat transmission component, the method comprising:

a) transmitting the diffusive heat transmission component by diffusion of the gaseous fluid through a sensor housing lid; and b) generating the convective heat transmission component by convection of fresh gaseous fluid by one of inflow and outflow of the fresh gaseous fluid via the heatable diaphragm;

wherein the fresh gaseous fluid flows through a housing of the sensor in a horizontal direction.

7. The method according to claim 6, wherein the method is for detecting $H_2$ in an $H_2$-air-$H_2O$ gas mixture.

* * * * *